United States Patent
Spindler et al.

(10) Patent No.: US 11,439,495 B2
(45) Date of Patent: Sep. 13, 2022

(54) SELF-HEALING GRAFT MATERIAL AND METHOD OF USE THEREOF

(71) Applicant: COOK MEDICAL TECHNOLOGIES LLC, Bloomington, IN (US)

(72) Inventors: Ralf Spindler, Solsberry, IN (US); Davorin Kevin Skender, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 509 days.

(21) Appl. No.: 16/545,311

(22) Filed: Aug. 20, 2019

(65) Prior Publication Data

US 2020/0060807 A1 Feb. 27, 2020

Related U.S. Application Data

(60) Provisional application No. 62/721,235, filed on Aug. 22, 2018.

(51) Int. Cl.

| | |
|---|---|
| *A61F 2/02* | (2006.01) |
| *A61F 2/06* | (2013.01) |
| *A61L 31/10* | (2006.01) |
| *C08L 75/04* | (2006.01) |
| *A61F 2/07* | (2013.01) |
| *C08L 77/00* | (2006.01) |
| *A61F 2/90* | (2013.01) |
| *C08G 18/28* | (2006.01) |
| *C08G 64/08* | (2006.01) |

(52) U.S. Cl.
CPC .............. *A61F 2/07* (2013.01); *A61F 2/90* (2013.01); *C08L 75/04* (2013.01); *C08L 77/00* (2013.01); *C08G 18/283* (2013.01); *C08G 64/081* (2013.01)

(58) Field of Classification Search
None
See application file for complete search history.

(56) References Cited

U.S. PATENT DOCUMENTS

| | | | |
|---|---|---|---|
| 5,948,018 | A | 9/1999 | Dereume et al. |
| 6,334,868 | B1 | 1/2002 | Ham |
| 6,702,849 | B1 | 3/2004 | Dutta et al. |

(Continued)

FOREIGN PATENT DOCUMENTS

| | | |
|---|---|---|
| CA | 2114891 C | 2/1994 |
| CA | 2340439 C | 8/2008 |

(Continued)

OTHER PUBLICATIONS

Y. Wu et al., Bioinspired supramolecular fibers drawn from a multiphase selfassembled hydrogel, PNAS, vol. 114, 31, 8163-8168, 2017, 6 pages.

(Continued)

*Primary Examiner* — Ann Schillinger
(74) *Attorney, Agent, or Firm* — Crowell & Moring LLP

(57) ABSTRACT

The present disclosure relates to a graft material including a self-healing polymer layer and to implantable medical devices including such a graft material. The invention also relates to methods of using and manufacturing such graft materials and devices. In one embodiment, the implantable medical device is a stent graft.

19 Claims, 1 Drawing Sheet

(56) References Cited

U.S. PATENT DOCUMENTS

| | | | |
|---|---|---|---|
| 6,800,089 B1 | 10/2004 | Wang | |
| 6,911,040 B2 | 6/2005 | Johnson et al. | |
| 7,118,592 B1 | 10/2006 | Dang et al. | |
| 7,288,112 B2 | 10/2007 | Denardo et al. | |
| 7,413,573 B2 | 8/2008 | Hartley et al. | |
| 7,538,180 B2 * | 5/2009 | Pacetti | A61L 31/10 528/480 |
| 7,749,263 B2 * | 7/2010 | DesNoyer | A61P 7/04 623/1.48 |
| 7,897,171 B2 * | 3/2011 | Strickler | A61L 27/16 525/308 |
| 8,309,112 B2 * | 11/2012 | Glauser | A61L 31/10 424/422 |
| 8,721,704 B2 | 5/2014 | Cully et al. | |
| 8,883,188 B2 | 11/2014 | Dankers et al. | |
| 9,339,593 B2 * | 5/2016 | Bjork, Jr. | A61L 31/16 |
| 9,687,591 B2 | 6/2017 | Hauser et al. | |
| 2002/0096252 A1 | 7/2002 | Lukic | |
| 2003/0158598 A1 * | 8/2003 | Ashton | A61L 31/10 623/1.42 |
| 2005/0131519 A1 | 6/2005 | Hartley | |
| 2005/0154445 A1 * | 7/2005 | Hunter | A61L 31/16 623/1.42 |
| 2008/0114096 A1 * | 5/2008 | Qu | A61L 31/10 427/457 |
| 2008/0175881 A1 * | 7/2008 | Ippoliti | A61L 31/16 424/423 |
| 2008/0175980 A1 * | 7/2008 | Sun | B05D 7/22 427/2.25 |
| 2008/0195193 A1 | 8/2008 | Purdy et al. | |
| 2008/0200377 A1 * | 8/2008 | Trollsas | A61K 9/5031 514/8.1 |
| 2009/0018643 A1 * | 1/2009 | Hashi | A61L 31/146 623/1.15 |
| 2014/0010858 A1 * | 1/2014 | Stankus | A61L 27/54 528/80 |
| 2015/0093574 A1 | 4/2015 | Tayi et al. | |
| 2015/0173921 A1 | 6/2015 | Lavrijsen et al. | |

FOREIGN PATENT DOCUMENTS

| | | | |
|---|---|---|---|
| WO | WO 97/17039 A1 | 5/1997 | |
| WO | WO 02/22024 A2 | 3/2002 | |
| WO | WO-2008076383 A2 * | 6/2008 | A61L 31/10 |
| WO | WO-2010112911 A2 * | 10/2010 | A61L 27/34 |
| WO | WO-2011007352 A2 * | 1/2011 | A61F 2/945 |
| WO | WO-2015058964 A1 * | 4/2015 | A01N 43/36 |
| WO | WO-2019147188 A1 * | 8/2019 | |

OTHER PUBLICATIONS

S. van der Zwaag (ed.), Self-Healing Materials: An Alternative Approach to 20 Centuries of Materials Science, Springer Series in Materials Science, 2007, pp. 1-68 and 95-138.

D.Y. Wu et al., Self-healing polymeric materials: A review of recent developments, Prog. Polym. Sci. 33 (2008) 479-522, 44 pages.

J. Wu et al., Tough self-healing elastomers by molecular enforced integration of covalent and reversible networks, Adv Mater. Aug. 11, 2017. Doi: 10.1002/adma.201702616 (Epub ahead of print), 32 pages.

V.K. Thakur et al., Self-healing polymer nanocomposite materials: A Review, http://dx.doi.org/10.1016/j.polymer.2015.04.086, ScienceDirect, Polymer 69 (2015) 369-383.

S.M. Kim et al., Superior Toughness and Fast Self-Healing at Room Temperature Engineered by Transparent Elastomers, Adv. Mater., 2017, 1705145, 8 pages.

* cited by examiner

SELF-HEALING GRAFT MATERIAL AND METHOD OF USE THEREOF

RELATED APPLICATIONS

This application claims the benefit of the filing date under 35 U.S.C. § 119(e) of Provisional U.S. Patent Application Ser. No. 62/721,235, filed Aug. 22, 2018, which is hereby incorporated by reference in its entirety.

TECHNICAL

The present disclosure relates to a graft material including a layer incorporating a self-healing material and to implantable medical devices including such a graft material. The invention also relates to methods of using and manufacturing such graft materials and devices. In one embodiment the device is a stent graft for placement is a vessel of the vascular system for treatment of coronary or peripheral artery disease in a patient.

BACKGROUND

Implantable medical devices, particularly endoluminally deployable medical devices, are known for a variety of medical applications, including the treatment of aneurysms. Aneurysms occur in blood vessels at sites where, due to age, disease or genetic predisposition, the strength or resilience of the vessel wall is insufficient to prevent ballooning or stretching of the wall as blood flows therethrough. If the aneurysm is left untreated, the blood vessel wall may expand to a point at which rupture occurs, often leading to death.

To prevent rupturing of an aneurysm, such as an abdominal aortic aneurysm, a stent graft may be introduced into a blood vessel percutaneously and deployed to span the aneurysmal sac. The outer surface of each end of the stent graft is preferably sealed against the interior wall of the blood vessel at a site where the interior wall has not suffered a loss of strength or resilience. Blood flowing through the vessel is channeled through the hollow interior of the stent graft to reduce, if not eliminate, the stress on the vessel wall at the location of the aneurysmal sac. Therefore, the risk of rupture of the blood vessel wall at the aneurysmal location is significantly reduced or eliminated, and blood can pass through the vessel without interruption.

Stent grafts include a graft fabric secured to a stent. The graft is typically inserted into or pulled over the stent and attached to its structural components. Alternatively, the stent may be formed on the graft such that the individual wires of the stent are threaded through specially provided projecting fabric loops on the surface of the graft. The stent provides rigidity and structure to hold the graft open in a tubular configuration as well as the outward radial force needed to create a seal between the graft and the vessel wall. The graft provides the tubular channel for blood flow past the aneurysm and prevents blood from pressurizing the aneurysmal sac.

However, current stent-graft materials are known to sometimes exhibit a lack of strength and are subject to rupture. This may have life-threatening consequences when devices incorporating such graft material rupture after being implanted.

SUMMARY

One aspect of the present invention provides a stent graft including an expandable stent and a graft having a layer including a self-healing polymer disposed on at least one of the luminal and the abluminal surface of the expandable stent.

In one embodiment, the self-healing polymer is a cross-linked co-polymer of a diamine and acrylic acid having a mixture of reversible hydrogen bonds and permanent covalent crosslinks. In such an embodiment, the diamine may be 1,12 diaminododecane.

In another embodiment, the self-healing polymer is a thermoplastic polyurethane comprising a hard segment component, a soft segment component and a chain extender component. The hard segment component may include a diisocyanate unit, for example isophorone diisocyanate, 4,4'-methylenebis(cyclohexyl isocyanate), 4,4' methylenebis (phenyl isocyanate) hexamethylene diisocyanate. The soft segment component may include polytetramethylene ether glycol. The chain extender component may include bis(4-hydroxyphenyl) disulphide.

In some embodiments, the graft further includes a second layer disposed on the first layer. The second layer may include a polymer, for example, polytetrafluoroethylene, electro-spun polytetrafluoroethylene, expanded polytetrafluoroethylene, polyethylene terephthalate, polyester, polyurethane or fluorinated ethylene propylene. In preferred embodiments, the second layer includes electro-spun polytetrafluoroethylene or expanded polytetrafluoroethylene.

In further embodiments, the self-healing graft includes a third layer comprising a polymer, for example, polytetrafluoroethylene, electro-spun polytetrafluoroethylene, expanded polytetrafluoroethylene, polyethylene terephthalate, polyester, polyurethane or fluorinated ethylene propylene. In one embodiment, the first layer is disposed between the second layer and the third layer.

The self-healing polymer material may be woven, knitted or braided. In other embodiments, the self-healing polymer material imbedded in another polymer, for example, polyurethane.

In another embodiment, the expandable stent includes a plurality of interconnected struts at least partially imbedded within the first layer. In another embodiment, the first layer attaches to the expandable stent by an adhesive or a suture. The struts may include a material such as nylon, a nickel-titanium alloy, stainless steel and a cobalt-chromium alloy.

In some embodiments the graft includes a plurality of stacked layers including the self-healing polymer material. At least one of the plurality of stacked layers is separated from another of the plurality of stacked layers by a layer including polytetrafluoroethylene, electro-spun polytetrafluoroethylene, expanded polytetrafluoroethylene, polyethylene terephthalate, polyester, polyurethane or fluorinated ethylene propylene.

Another aspect of the present invention provides a graft material comprising a first layer including a self-healing polymer material and a second layer including polytetrafluoroethylene, electro-spun polytetrafluoroethylene, expanded polytetrafluoroethylene, polyethylene terephthalate, polyester, polyurethane or fluorinated ethylene propylene. The second layer is disposed on the first layer.

In one embodiment, the self-healing polymer is a cross-linked co-polymer of a diamine and acrylic acid as disclosed herein. In another embodiment, the self-healing polymer is a thermoplastic polyurethane as disclosed herein.

In some embodiments, the graft also includes a third layer including polytetrafluoroethylene, electro-spun polytetrafluoroethylene, expanded polytetrafluoroethylene, polyethylene terephthalate, polyester, polyurethane or fluorinated ethylene propylene. The first layer may be disposed between the second layer and the third layer.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
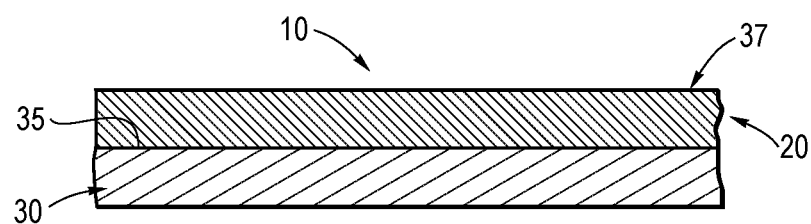
FIG. 1 is a schematic illustration showing one embodiment of a graft of the present invention.

It is to be understood that the drawings are schematic only and not to scale. Often only the principal components relevant to the teachings herein are shown in the drawings, for the sake of clarity.

The term "implantable medical device" refers to a medical device that is permanently or temporarily inserted into a patient's body for treatment of a medical condition.

The term "luminal surface," as used herein, refers to the portion of the surface area of a medical device defining at least a portion of an interior lumen. Conversely, the term "abluminal surface," refers to portions of the surface area of a medical device defining at least a portion of an exterior surface of the device. For example, where the medical device is a stent-graft having a stent portion with a cylindrical frame formed from a plurality of interconnected struts and bends defining a cylindrical lumen, the abluminal surface can include the exterior surface of the stent, or grant, i.e. those portions of the stent or graft that are placed adjacent or in contact with the vessel wall when the stent-graft is expanded, while the luminal surface can include the interior surface of the struts and bends or covering, i.e. those portions of the device that are placed adjacent or in contact with the vessel interior when the stent-graft is expanded.

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a therapeutic agent means an amount of the therapeutic agent which imparts a therapeutic effect to the human or veterinary patient.

The term "self-healing polymer" as used herein means a polymer material that reverts to its original state after damage.

Self-Healing Graft Material

Aspects of the present invention provide a graft including a self-healing polymer and implantable medical devices incorporating such a graft. In certain embodiments, the graft is in the form of a single layer sheet including the self-healing polymer, and optionally other materials (self-healing layer). In other embodiments, the graft is a multilayered structure including a layer containing the self-healing polymer and at least one other layer, the other layer(s) not including the self-healing polymer.

In one embodiment, the self-healing polymer is a crosslinked co-polymer of a diamine and acrylic acid having a mixture of reversible hydrogen bonds and permanent covalent crosslinks. The diamine may be, for example, 1,12 diaminododecane. Unlike classical polymer networks that are crosslinked by permanent covalent bonds, prior self-healing polymeric materials are often based on reversible associations, such as hydrogen bonding. Such reversible associations can break and reform to enable self-healing ability, but they are weak compared to covalent bonds. This causes the toughness of self-healing polymers not to match that of covalent polymer networks. Introducing permanent, covalent crosslinks into a reversible network improves its mechanical properties.

In one embodiment, the polymer includes covalent crosslinks formed by condensation between amine groups of the diamine and carboxyl groups of the acrylic acid. The randomly branched polymer links these two types of bonds and forces them to mix on the molecular level without macroscopic phase separation. This allows the creation of a homogenous, optically transparent dry elastomer without co-solvents. At small deformations, the hydrogen bonds break and reform to dissipate energy. At large deformations, the hybrid elastomer exhibits patterns that help maintain material integrity. The ability to deform hydrogen bonds at small deformations and maintain material integrity at large deformations produces a very tough elastomer with fracture energy comparable to that of natural rubber. Moreover, the hybrid elastomer self-heals at room temperature with a recovered tensile strength comparable or better to the existing self-healing elastomers. Such polymers may be produced used the method of Wu, J. et al. "Tough self-heating elastomers by molecular enforced integration of covalent and reversible networks", Adv Mater, August 11. Doi: 10:1002/ama.201702616.

In another embodiment, the self-healing polymer is a thermoplastic polyurethane. Typically, polyurethanes are made by combining a diol component, a diisocyanate component and a chain extender component. Generally, polyurethanes contain a soft (rubbery) and a hard (crystalline) component. The properties of polyurethane depend on the nature and relative concentration of the soft/hard components. A thermoplastic polyurethane having self-healing properties may be produced by the method of Seon-Mi Kim et al. "Superior Toughness and Fast Self-Healing at Room Temperature Engineered by Transparent Elastomers" Adv. Mater. 2017 1705145.

In one embodiment, the soft segment unit is polytetramethylene ether glycol (PTMEG). In other embodiments, the hard segment unit is a diisocyanate, such as isophorone diisocyanate, 4,4'-methylenebis(cyclohexyl isocyanate), 4,4' methylenebis(phenyl isocyanate) or hexamethylene diisocyanate. In a preferred embodiment, the hard segment unit is isophorone diisocyanate. The self-healing polymer may be synthesized by first reacting PTMEG (as a soft segment diol) with two equivalents of the diisocyanate monomer in N,N'-dimethylacetamide in the presence of dibutyltin dilaurate as a catalyst to form a bis-isocyanate-terminated preoligomer. Then, bis(4-hydroxyphenyl) disulfide is added to the solution as a chain extender to complete the thermoplastic polyurethane synthesis.

Graft Materials Incorporating a Self-Healing Polymer

The layer(s) incorporating the self-healing polymer and other layers present in the graft material may be attached to each other by, for example, pressing the two of more layers together at an elevated temperature. In such a procedure, the temperature should be such that at least one of the layers undergoes at least a limited melting, resulting in a bonding of the layers. In other embodiments, the layers are attached by an adhesive.

In some embodiments, the self-healing polymer is present in the form of fibers or in the form of strands containing multiple fibers. In other embodiments, the fibers, or strands of the fibers, are incorporated into a fabric, for example a knitted, woven or mesh textile material. In yet other embodiments, fibers or strands including self-heating polymer are present between strands of a knitted, woven or mesh textile material formed from another polymeric material.

In one embodiment, each individual strand incorporating the self-healing polymer is formed entirely from the self-heating polymer. In other embodiments, such strands include additional materials as well as the self-healing polymer. For example, an individual strand may be formed from fibers of the self-healing polymer without the presence of another material.

For example, the self-healing polymer may be coated onto a fibers or strands formed from another polymer. In one embodiment, such fibers or strands are used to weave a textile material. The strands may be loosely packed or twisted such that the self-healing polymer is contained within the strand. In other embodiments, each individual strand is formed from a combination of fibers of the self-heating polymer and fibers of another natural or synthetic material, such as those disclosed herein. Each strand may be formed of at least two, three, four, five, six or more fibers aligned with or without a twist. For example, a strand may be formed of one or more fibers of the self-heating polymer combined with one or more fibers formed from another material.

In one embodiment, the self-heating polymer is continuously integrated along the strand of the material. In yet another embodiment, the self-heating polymer is discontinuously integrated along the strand in combination with filaments of other materials.

In some embodiments, the fibers or strands including the self-healing polymer are deposited to form a matrix at least partially embedded between strands of a woven, knitted or mesh material formed from a natural or synthetic textile material. Example of such synthetic materials include, for example, polyesters, such as poly(ethylene terephthalate); fluorinated polymers, such as polytetrafluoroethylene (PTFE) and fibers of expanded PTFE; polyethylene, polypropylene, polyaramids, polyacrylonitrile, nylons and polyurethanes. In addition, materials that are not inherently biocompatible may be suitable for use as textile strands if they can be rendered biocompatible. For example, surface modification techniques may be employed to impart biocompatibility to such materials. Examples of surface modification techniques include graft polymerization of biocompatible polymers from the material surface, coating of the surface with a crosslinked biocompatible polymer, chemical modification with biocompatible functional groups, and immobilization of a compatibilizing agent such as heparin or other substances.

In other embodiments, the self-healing polymer is not formed into a strand but is instead present as a film or as a matrix material incorporated into a mesh of a textile material. For example, a sheet or film of the self-healing polymer may be shredded into smaller pieces that are used as a binder between the pores of a knitted or woven textile.

In certain embodiments, the graft may include multiple layers including the self-healing polymer and/or other layers. For example, a layer including the self-healing polymer may be positioned between two other layers to form a multilayered graft. More complex grafts may be formed, including grafts with multiple altering self-heating polymer layers and other layers not including the self-healing polymer. For example, the graft may include 2, 3, 4, 5, 6, 7, 8, 9, 10 or more self-heating polymer layers. In such embodiments, each self-heating polymer layer is separated from and attached to another self-heating polymer layer by an intervening layer not including the self-heating polymer. In other embodiments, the graft may include two, three, four, five or more layers including the self-heating polymer attached directly to each other. In such embodiments, these layers may include additional materials as disclosed herein, with the same or different additional material being included in each layer.

The other layers present in the graft may be porous layers and, in certain embodiments, one of these layers forms the outermost layer of the graft. For example, when the graft is utilized as the graft of a vascular stent-graft device, this outermost layer may form the abluminal surface of the device and be placed in contact with the blood vessel wall when the stent-graft device is implanted in the body of a patient. In such embodiments, the porous layer allows for cellular migration when the device is implanted.

In some embodiments, the other layers of the graft are formed from a polymeric material such as polyethylene, polypropylene, polyaramids, polyacrylonitrile, nylons, cellulose, polyester, a fluorinated polymer or polyurethane, polytetrafluoroethylene, electro-spun polytetrafluoroethylene, expanded polytetrafluoroethylene, polyethylene terephthalate, polyester, polyurethane, fluorinated ethylene propylene or combinations or copolymers of these materials In certain embodiments, the other layer(s) include at least one of electrospun polytetrafluoroethylene "(esPTFE") and expanded polytetrafluoroethylene ("ePTFE"). Preferably, the layer is formed from only one of these materials. esPTFE is formed by the use of an electric force to draw charged threads of PTFE polymer solutions or polymer melts up to fiber diameters in the order of some hundred nanometers.

ePTFE has a micro-structure characterized by nodes interconnected by fibrils of the polymer. The material is formed by expanding paste-formed products of a tetrafluoroethylene polymer to form a material having high porosity and high strength. The fibrils of the polymer are substantially orientated in the direction of the expansion of the material. Both esPTFE and ePTFE materials are commercially available in sheet form from, for example, Zeus Industrial Products, Inc., Orangeburg, S.C. 29115.

In those embodiments where the graft includes multiple layers of ePTFE, the orientation of the individual layers of ePTFE within the graft may vary with respect to the direction of expansion (and fibril orientation) of the ePTFE. For example, some embodiments may include an ePTFE layer positioned with the direction of expansion parallel to an axis of the device and another ePTFE layer positioned with the direction of expansion positioned at an angle, for example perpendicular to, that axis.

In other embodiments, the graft may include a "mat" layer that provides for additional load bearing capacity to the graft. In such embodiments, the mat layer may be attached to the reinforced graft material layer and/or to a layer not including the self-healing polymer. The graft may include 1, 2, 3, 4, or more mat layers. In some embodiments, the mat layer is a mesh or a braided, woven or knitted layer. The mat layer may be formed from, for example, polyether ether ketone (PEEK), Polyethylene terephthalate (PETE), ultra-high-molecular-weight polyethylene (UHMWPE), nylon, or a metallic material, such as a super-elastic nickel-titanium alloy (e.g. NITINOL), stainless steel, gold, platinum, palladium, titanium, tantalum, tungsten, molybdenum, cobalt-chromium alloy, such as L-605, MP35N, Elgiloy; nickel-chromium alloys, such as alloy 625; and niobium alloys, such as Nb-1% Zr.

Implantable Devices Incorporating a Self-Healing Graft Material

The self-healing graft may form part of implantable medical devices such as, but not limited to, endovascular grafts, vascular grafts, stent grafts, balloon catheters, meshes, filters (e.g., vena cava filters), tissue scaffolds, myocardial plugs, valves (e.g., venous valves), pelvic implants, various types of dressings, or other known implantable devices, including flat sheet structures such as hernia patches, skin graft patches, bone stabilization devices or bandages.

The medical device may be a bifurcated integrated stent-graft, an integrated stent-graft configured for any blood vessel including coronary arteries and peripheral arteries (e.g., renal, superficial femoral, carotid, and the like), a urethral integrated stent-graft, a biliary integrated stent-graft, a tracheal integrated stent-graft, a gastrointestinal integrated stent-graft, or an esophageal integrated stent-graft, for example.

Typically, in stent-graft devices, the graft attaches to the stent portion of the devices by, for example, sutures or an adhesive, so that when the stent is expanded alter delivery to the treatment site, the fabric material contacts the vessel wall and provides support for any weakness present.

In preferred embodiments, a graft as described herein attaches to a balloon expandable or self-expanding stent to form a stent-graft device. The stent portion of the device is generally formed of at least one tubular portion and may be configured as a unitary structure or as a plurality of attached portions, for example, attached tubular portions or a plurality of interconnected struts, which may collectively define the stent portion. The tubular portion may be made from a woven or knitted structure, a laser-cut cannula, individual interconnected rings, or another pattern or design.

The stent portion may be formed from a metallic material such as stainless steel, super-elastic nickel-titanium (NITINOL), silver, platinum, palladium, gold, titanium, tantalum, iridium, tungsten, cobalt, chromium, cobalt-chromium alloy, cobalt-based alloy, nickel-based alloy or molybdenum alloy. Biodegradable metals may also be used, including, for example, a biodegradable magnesium alloy.

In other embodiments, the stent portion may by formed from a biodegradable or non-biodegradable polymeric material. Nonbiodegradable polymers that can be used include for example cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures of these materials. Biodegradable polymers that can be used include for instance polylactic acid (PLA), polyglycolic acid (PGA), poly(lactic-co-glycolic acid) (PLGA), polyanhydride, polycaprolactone, polyhydroxybutyrate valerate, or mixtures of these materials.

The self-healing graft may be attached to the stent portion of the device by, for example, adhesive, sutures, staples or clips. Alternatively, or as well as, the stent portion of the stent-graft may be at least partially imbedded into one of the self-healing layers of the graft. In other embodiments, the stent portion of the stent-graft is at least partially imbedded into one of the layers not including the self-healing polymer.

Non limiting examples of grafts as disclosed herein and stent-graft devices incorporating such grafts will now be illustrated with reference to FIGS. 1 to 3. Referring first to the FIG. 1, which is a schematic illustration of a cross-sectional view of one embodiment of a graft of the present invention. In this embodiment, graft 10 is a two-layered structure including a self-healing layer 20 having a first surface 35 attached to a second layer 30. In this embodiment, second layer 30 does not include the self-healing polymer. In another embodiment, the graft includes a third layer (not illustrated) attached to second surface 37 of self-healing layer 20. In some embodiments, the second and/or third layers may be formed from, for example, esPTFE, ePTFE polymer or from any of the other polymeric materials disclosed herein.

Figure 2:
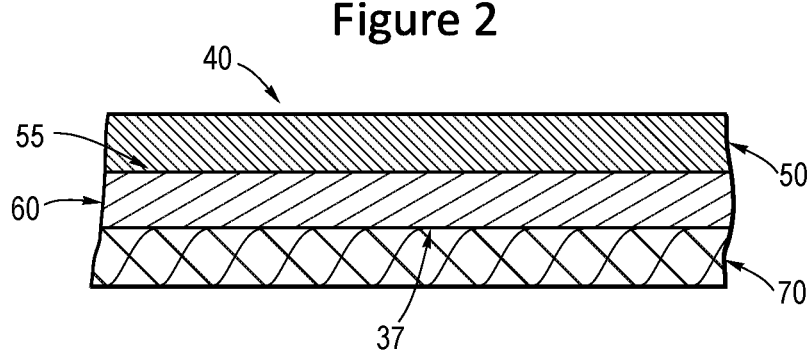
FIG. 2 is a schematic illustration showing another embodiment of a graft of the present invention.

FIG. 2 is a schematic illustration showing a cross-sectional view of another embodiment of a self-healing graft. In this embodiment, graft 40 is a three-layered structure including layer 50 bonded to a first surface 55 of self-healing layer 60. Layer 50 may be formed from, for example, esPTFE, ePTFE polymer or from any of the other polymeric materials disclosed herein. Layer 70 attaches to a second surface 37 of self-healing layer 60 and may be a "mat" layer as disclosed herein.

Figure 3:
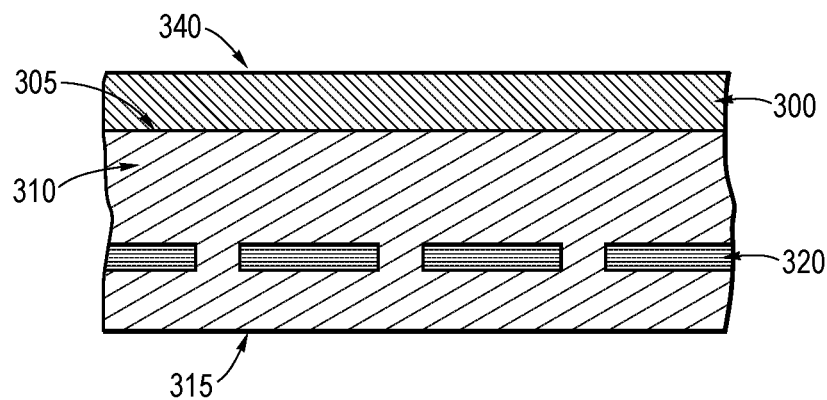
FIG. 3 is a schematic illustration showing an embodiment of part of a stent-graft including one embodiment of a graft of the present invention.

FIG. 3 shows a cross-sectional view of a portion of one embodiment of a stent-graft including a self-healing graft as disclosed herein. Stent-graft 340 includes stent portion 320, which in imbedded within layer 310, which may include a self-healing polymer. Layer 300 attaches to surface 305 of 310 and may form the luminal or the abluminal surface of stent-graft device 340. In other embodiments, a third layer (not illustrated) lay be attached to second surface 315 of layer 310.

Implantable Devices Incorporating a Bioactive Agent

The grafts and implantable medical devices disclosed herein may also include a therapeutically effective amount of a bioactive agent. For example, the bioactive agent may be incorporated into the graft and/or into another component of the device. For example, in the case of stent-graft devices, the bioactive agent may be incorporated into the one or more layers of the graft. The bioactive material may be incorporated during the manufacturing process used for form the individual layers of the graft, for example when forming the reinforcement, mat and/or bonding layers. In other embodiments, the bioactive agent may be impregnated into the graft after it has be formed by combining the individual layers.

The bioactive agent may be selected to perform a desired function upon implantation. Bioactive agents within the scope of the present embodiments include antiproliferative agents immunosuppressive agents, restenosis-inhibiting agents, anti-cancer agents, analgesics/antipyretics, anesthetics, antiasthmatics, antibiotics, antidepressants, antidiabetics, antifungal agents, antihypertensive agents, anti-inflammatories, antineoplastics, antianxiety agents, sedatives/hypnotics, antianginal agents, nitrates, antipsychotic agents, antimanic agents, antiarrhythmics, antiarthritic agents, antigout agents, thrombolytic agents, hemorheologic agents, anticonvulsants, antihistamines, agents useful for calcium regulation, antibacterial agents, antiviral agents, antimicrobials, anti-infectives, bronchodilators, steroids and hormones.

Non-limiting examples of such drugs include doxorubicin, camptothecin, etoposide, mitoxantrone, cyclosporine, epothilones, napthoquinones, 5 fluorouracil, methotrexate, colchicines, vincristine, vinblastine, gemcitabine, statins (for example atorvastatin, fluvastatin, lovastatin, pitavastatin, pravastatin, rosuvastatin and simvastatin), steroids (for example cortisteroids, prednisilone and dexamethazone) mitomycin and derivatives or analogues of these agents.

Preferred bioactive agents include restenosis-inhibiting agents a, including but not limited to microtubule stabilizing agent such as paclitaxel, a paclitaxel analog, or a paclitaxel derivative or other taxane compound; a macrolide immunosuppressive agent such as sirolimus (rapamycin), pimecrolimus, tacrolimus, everolimus, zotarolimus, novolimus, myolimus, temsirolimus, deforolimus, or biolimus; an antiproliferative agent; a smooth muscle cell inhibitor; an inhibitor of the mammalian target of rapamycin (mTOR inhibitor).

Certain bioactive agents may be present in more than one polymorphic form. For example, paclitaxel may be present as at one of Solid forms of amorphous paclitaxel ("aPTX"), dihydrate crystalline paclitaxel ("dPTX") and anhydrous crystalline paclitaxel.

Although the invention has been described and illustrated with reference to specific illustrative embodiments, it is not intended that the invention be limited to these illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A stent graft comprising:
   an expandable stent having a luminal and an abluminal surface; and
   a graft disposed on at least one of the luminal and the abluminal surface;
   wherein the graft comprises a first layer comprising a self-healing polymer material; and wherein the self-healing polymer is a cross-linked co-polymer of a diamine and acrylic acid having a mixture of reversible hydrogen bonds and permanent covalent crosslinks.

2. The stent-graft of claim 1, wherein the diamine is 1,12 diaminododecane.

3. The stent-graft of claim 1 further comprising a second self-healing polymer layer, wherein the second self-healing polymer is a thermoplastic polyurethane comprising a hard segment component, a soft segment component and a chain extender component.

4. The stent-graft of claim 3, wherein the hard segment component comprises a polymerized diisocyanate unit, wherein the diisocyanate is selected from the group consisting of isophorone diisocyanate, 4,4'-methylenebis(cyclohexyl isocyanate), 4,4' methylenebis(phenyl isocyanate) and hexamethylene diisocyanate.

5. The stent-graft of claim 3, wherein the soft segment component comprises polymerized polytetramethylene ether glycol.

6. The stent-graft of claim 3, wherein the chain extender component comprises polymerized bis(4-hydroxyphenyl) disulphide.

7. The stent-graft of claim 1, wherein the graft further comprises a second layer comprising a polymer selected from the group consisting of polytetrafluoroethylene, electro-spun polytetrafluoroethylene, expanded polytetrafluoroethylene, polyethylene terephthalate, polyester, polyurethane and Fluorinated ethylene propylene, and wherein the second layer is disposed on the first layer.

8. The stent graft of claim 7, wherein the graft further comprises a third layer comprising a polymer selected from the group consisting of polytetrafluoroethylene, electro-spun polytetrafluoroethylene, expanded polytetrafluoroethylene, polyethylene terephthalate, polyester, polyurethane and fluorinated ethylene propylene, wherein the first layer is disposed between the second layer and the third layer.

9. The stent-graft of claim 1, wherein the self-healing polymer material is woven, knitted or braided, and, wherein the self-healing polymer material imbedded in a polyurethane.

10. The stent graft of claim 1, wherein the expandable stent comprises a plurality of interconnected struts at least partially imbedded within the first layer.

11. The stent-graft of claim 1, wherein the graft comprises a plurality of stacked layers the self-healing polymer material, wherein at least one of the plurality of stacked layers is separated from another of the plurality of stacked layers by a layer comprising a polymer selected from the group consisting of polytetrafluoroethylene, electro-spun polytetrafluoroethylene, expanded polytetrafluoroethylene, polyethylene terephthalate, polyester, polyurethane and fluorinated ethylene propylene.

12. A stent graft comprising a stent and graft material, the graft material comprising a first layer comprising a self-healing polymer material and a second layer comprising a polymer selected from the group consisting of polytetrafluoroethylene, electro-spun polytetrafluoroethylene, expanded polytetrafluoroethylene, polyethylene terephthalate, polyester, polyurethane and fluorinated ethylene propylene, wherein the second layer is disposed on the first layer; and wherein the self-healing polymer is a cross-linked co-polymer of a diamine and acrylic acid having a mixture of reversible hydrogen bonds and permanent covalent crosslinks.

13. The stent-graft of claim 12, wherein the diamine is 1,12 diaminododecane.

14. The stent-graft of claim 12 further comprising a second self-healing polymer layer, wherein the second self-healing polymer is a thermoplastic polyurethane comprising a hard segment component, a soft segment component and a chain extender component.

15. The stent-graft of claim 14, wherein the hard segment component comprises a polymerized diisocyanate unit, wherein the diisocyanate is selected from the group consisting of isophorone diisocyanate, 4,4'-methylenebis(cyclohexyl isocyanate), 4,4' methylenebis(phenyl isocyanate) and hexamethylene diisocyanate.

16. The stent-graft of claim 14, wherein the soft segment component comprises polymerized polytetramethylene ether glycol.

17. The stent-graft of claim 14, wherein the chain extender component comprises polymerized bis(4-hydroxyphenyl) disulphide.

18. The stent-graft of claim 12, wherein the graft further comprises a third layer comprising a polymer selected from the group consisting of polytetrafluoroethylene, electro-spun polytetrafluoroethylene, expanded polytetrafluoroethylene, polyethylene terephthalate, polyester, polyurethane and fluorinated ethylene propylene, wherein the first layer is disposed between the second layer and the third layer.

19. A stent graft comprising:
   an expandable stent comprising a tubular body with a lumen extending therethrough and having a luminal and an abluminal surface; and
   a graft disposed on at least one of the luminal and the abluminal surface;
   wherein the graft comprises:
   a first layer comprising self-healing polymer, wherein the self-healing polymer is a cross-linked co-polymer of a diamine and acrylic acid having a mixture of reversible hydrogen bonds and permanent covalent crosslinks;
a second layer comprising electro-spun polytetrafluoroethylene or expanded polytetrafluoroethylene; and
a third layer comprising electro-spun polytetrafluoroethylene or expanded polytetrafluoroethylene,
wherein the first layer is disposed between the second layer and the third layer.

* * * * *